US00PP14906P2

(12) United States Plant Patent
Ware

(10) Patent No.: US PP14,906 P2
(45) Date of Patent: Jun. 15, 2004

(54) COPROSMA PLANT NAMED 'FIRE BURST'

(50) Latin Name: *Coprosma hybrida*
Varietal Denomination: Fire Burst

(76) Inventor: Richard G. Ware, Oak Road, R.D. 2, Napier (NZ)

( * ) Notice: Subject to any disclaimer, the term of this patent is extended or adjusted under 35 U.S.C. 154(b) by 0 days.

(21) Appl. No.: 10/624,105

(22) Filed: Jul. 21, 2003

(51) Int. Cl.[7] ..... A01H 5/00
(52) U.S. Cl. ..... Plt./226
(58) Field of Search ..... Plt./226

(56) References Cited

PUBLICATIONS

UPOV–ROM GTITM Computer Database, 2003/05, GTI Jouve Retrieval Software, citation 'Fire Burst'.*

* cited by examiner

*Primary Examiner*—Anne Marie Grunberg
*Assistant Examiner*—Susan McCormick
(74) *Attorney, Agent, or Firm*—C. A. Whealy

(57) ABSTRACT

A distinct cultivar of Coprosma plant named 'Fire Burst', characterized by its upright and somewhat outwardly spreading plant form; freely branching growth habit; and dark green, pale pink and bright ed tri-colored foliage.

1 Drawing Sheet

Botanical classification/cultivar designation: Coprosma hybrida cultivar Fire Burst.

BACKGROUND OF THE INVENTION

The present Invention relates to a new and distinct cultivar of Coprosma plant, botanically known as Coprosma hybrida, and hereinafter referred to by the name 'Fire Burst'.

The new Coprosma was discovered by the Inventor in 1999 in a controlled environment in Palmerston North, New Zealand, as a naturally-occurring whole plant mutation of the Coprosma hybrida cultivar Rainbow Surprise, not patented. The new Coprosma was selected by the Inventor on the basis of its uniquely-colored foliage.

Asexual reproduction of the new Coprosma by cuttings in a controlled environment in Palmerston, New Zealand since Aug. 10, 1999, has shown that the unique features of this new Coprosma are stable and reproduced true to type in successive generations.

SUMMARY OF THE INVENTION

Plants of the cultivar Fire Burst have not been observed under all possible environmental conditions. The phenotype may vary somewhat with variations in environment such as temperature and light intensity without, however, any variance in genotype.

The following traits have been repeatedly observed and are determined to be the unique characteristics of 'Fire Burst'. These characteristics in combination distinguish 'Fire Burst' as a new and distinct cultivar:

1. Upright and somewhat outwardly spreading plant form.
2. Freely branching growth habit.
3. Dark green, pale pink and bright red tri-colored foliage.

Plants of the cultivar Fire Burst are most similar to plants of the parent, the cultivar Rainbow Surprise. Plants of the new Coprosma differ from plants of the cultivar Rainbow Surprise in foliage coloration as plants of the new Coprosma have leaves with dark green-colored centers and bright red-colored margins whereas plants of the cultivar Rainbow Surprise have leaves with medium green-colored centers and bright pink-colored margins.

BRIEF DESCRIPTION OF THE PHOTOGRAPHS

The accompanying colored photographs illustrate the overall appearance of the new Coprosma, showing the colors as true as it is reasonably possible to obtain in colored reproductions of this type. Colors in the photographs may differ slightly from the color values cited in the detailed botanical description which accurately describe the colors of the new Coprosma.

The photograph at the top of the sheet comprises a side perspective view of a typical plant of 'Fire Burst' grown in a container.

The photograph at the bottom of the sheet is a close-up view of typical leaves of 'Fire Burst'.

DETAILED BOTANICAL DESCRIPTION

In the following description, color references are made to The Royal Horticultural Society Colour Chart, 2001 Edition, except where general terms of ordinary dictionary significance are used. Plants used for the photographs and the following description where about three years old and grown under outdoor field conditions which closely approximate commercial production conditions in Boskoop, The Netherlands. The photographs and description were taken in December, 2002. At this time, day temperatures ranged from −4 to 4° C. and night temperatures ranged from −8 to 3° C.

Botanical classification: Coprosma hybrida cultivar Fire Burst.

Parentage: Naturally-occurring whole plant mutation of the Coprosma hybrida cultivar Rainbow Surprise, not patented.

Propagation:

*Type.*—By tip cuttings.

*Time to initiate roots.*—Summer: About 18 days at 25° C. Winter: About 15 days at 15° C.

*Time to produce a rooted cutting.*—Summer: About 118 days at 25° C. Winter: About 215 days at 25° C.

*Root description.*—Fibrous; medium to fine in thickness; wiry.

Plant description:

*Form.*—Perennial evergreen shrub; upright and somewhat outwardly spreading; inverted triangle, broadly upright plant form; freely branching, dense and bushy habit; moderately vigorous.

*Plant height.*—About 35 cm.

*Plant diameter.*—About 31 cm.

*Lateral branches.*—Quantity per plant: About 17; pinching is not required, but will improve branching. Length: About 15.4 cm. Diameter: About 2.5 mm. Internode length: About 1.5 mm. Strength: Strong. Texture: Smooth; glabrous. Color, young: 143B. Color, mature: 197A to 197C.

*Foliage description.*—Arrangement: Opposite, simple; sessile. Length: About 2.7 cm. Width: About 1 cm. Shape: Obovate. Apex: Obtuse. Base: Cuneate. Margin: Entire; slightly wavy. Texture, upper and lower surfaces: Thick, leathery; smooth, glabrous. Luster: glossy. Venation pattern: pinnate. Color: Developing foliage, upper surface: Towards the base, 143A; towards the apex, 147A to 139A; surrounded by 39C; towards margins, 53D. Developing foliage, lower surface: Between 189A and 191A. Fully expanded foliage, upper surface: Center, between 137A and 139A; surrounded by 31B; towards margins, 53D. Fully expanded foliage, lower surface: 191A; towards margins, 37B. Venation, upper surface: Midvein, 137A; lateral veins, same as lamina. Venation: lower surface: 191A.

*Stipules.*—Arrangement: Two minute stipules at leaf base. Length: About 3 mm. Width: About 1 mm. Shape: Narrowly oblanceolate. Color: 191B overlain with slight reddish tint.

Flower description: Flower development has not been observed.

Disease/pest resistance: Plants of the new Coprosma have not been noted to be resistant to pathogens and pests common to Coprosma.

Temperature tolerance: Plants of the new Coprosma are hardy to USDA Zones 8 to 9 and have been observed to tolerate temperatures as high as 35° C.

It is claimed:

1. A new and distinct cultivar of Coprosma plant named 'Fire Burst', as illustrated and described.

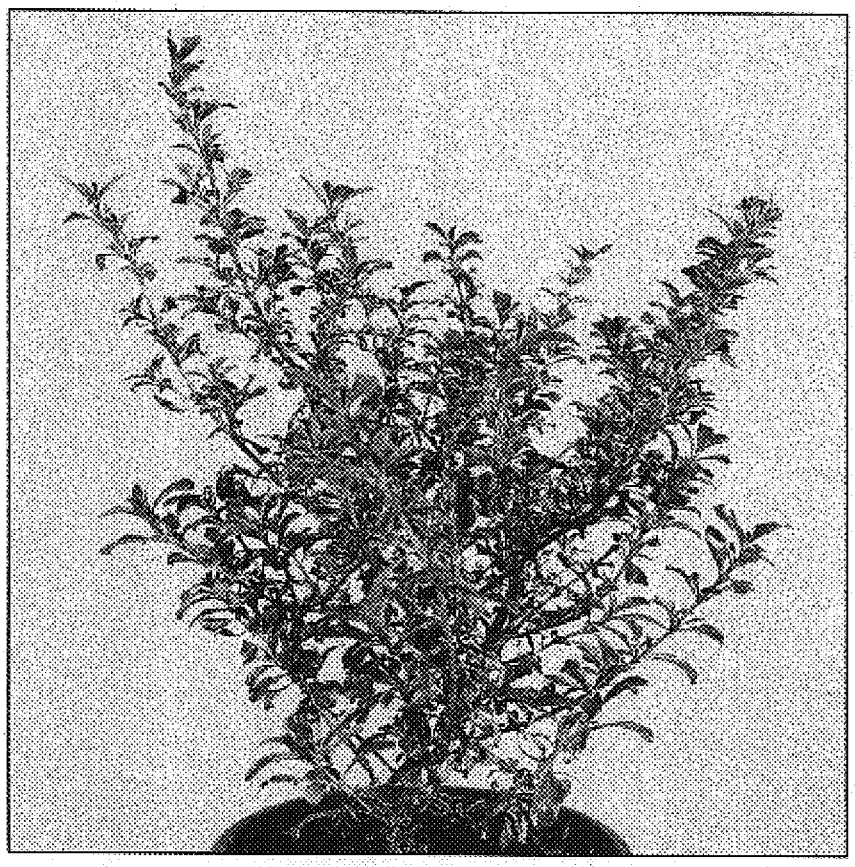
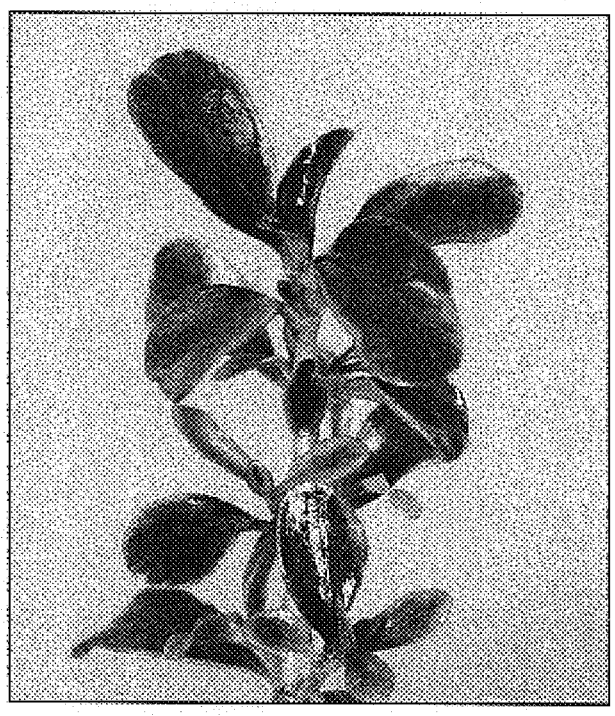

* * * * *